US00PP10446P

United States Patent [19]

Lemon

[11] Patent Number: Plant 10,446

[45] Date of Patent: Jun. 9, 1998

[54] VARIETY OF GERANUIM PLANT 'MAIDEN ORANGE'

[75] Inventor: David Lemon, Lompoc, Calif.

[73] Assignee: John Bodger & Sons Company, So. El Monte, Calif.

[21] Appl. No.: 724,706

[22] Filed: Oct. 1, 1996

[51] Int. Cl.[6] ..... A01H 5/00

[52] U.S. Cl. ..... Plt./87.12

[58] Field of Search ..... Plt./87.12

*Primary Examiner*—Howard J. Locker

*Attorney, Agent, or Firm*—Fulwider Patton Lee Lee Utecht, LLP

[57] ABSTRACT

The cultivar is characterized by its compact medium green foliage and soft orange bloom. Its strong growth habit, quick rooting time and continuous flowering provide for superb cuttings and also for quick recovery following wet weather conditions. The blooms exhibit good post-harvest quality.

1 Drawing Sheet

BACKGROUND OF THE NEW PLANT

The present invention comprises a new and distinct cultivar of *Pelargonium×domesticum* known by the varietal name Maiden Orange (Oglevee No. 714, Bodger No. 2 PD 17-12). The new variety was discovered in a selective breeding program by David Lemon at Bodger Seeds, Ltd., Lompoc, Calif. The new variety is a selection from the crossing of Walters Lavender (unpatented) which has a light rose-purple flower with dark purple markings and dark green leaves, with Bodger No. 8 PD 24-1 (unpatented) which is bi-colored seedling having medium green foliage, as compared to the claimed cultivar which has an orange flower with rich red and bright light pink markings with a medium green foliage.

The new cultivar was first asexually reproduced by cuttings at Oglevee Ltd., Connellsville, Pa., and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa., using full light, 60° Fahrenheit night temperature, 68° Fahrenheit day temperature, and grown in a soilless media of constant fertilizer 150–200 parts per million of nitrogen and potassium has a response time of fourteen weeks from the rooted cutting to a flowering plant in a 6 inch pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings believed to have been potted on approximately Feb. 1, 1996 and flowering on approximately Apr. 25, 1996 under full light and greenhouse, and colorings were taken indoors under 200–220 foot candles of fluorescent cool white light using the R.H.S. Colour Chart of The Royal Horticultural Society of London.

The Plant

Classification:
- *Botanical.*—*Pelargonium×domesticum.*
- *Commercial.*—Regal Geranium Maiden Orange.

Form: Compact mound.
- *Height.*—16.0–18.0 cm above media.
- *Growth.*—Controlled.
- *Strength.*—Fast rooting, compact sturdy growth — no support needed.

Foliage: Stalked leaf attachment.

Leaves:
- *Size.*—6.0–7.5 cm.
- *Shape.*—Depressed ovate, cordate base.
- *Margin.*—Serrate margin.
- *Texture.*—Leathery, slightly pubescent.
- *Color.*—Top: Yellow-green group 146 B.
  - Bottom: Yellow-green group 148 B.
  - Zone: None.
- *Ribs and veins.*—Palmate venation: Color: Yellow/green group 147C.

Petioles:
- *Length.*—5.0–6.5 cm.
- *Color.*—Yellow/green group 146C.

Stem:
- *Color.*—Yellow/green group 146D.
- *Internodes.*—1.5–2.0 cm.

The Bud (Umbell)

Shape: Elliptical cluster.

Size: 2.0–2.5 cm.

Inflorescence

Blooming habit: Continuous.

Borne: Umbel; florets on pedicel; pedicel on peduncle.

Closed florets:
- *Bud size.*—1.0–1.5 cm length,0.5cm width.
- *Size.*—Fully open bloom 7.5–8.5 cm across.

Open florets:
- *Form.*—Cupped.
- *Color.*—Top: Red group 43C. Bottom: Red group 50C. Eye: Red group 53A a darker eye appearing on the top two petals.
- *Petals.*—Five.
- *Size.*—4.0–5.0 cm across.
- *Texture and appearance.*—Smooth satiny; appearance from a distance is a soft orange bloom above compact medium green foliage.

Petaloids:
*Quantity.*—None.
Pedicel:
*Length.*—1.5 cm.
*Color.*—Yellow-Green Group 146D.
Peduncle:
*Length.*—3.0–4.0 cm.
*Color.*—Yellow-green group 146B.
Persistence:
*Disease resistance.*—Not known.
*Lasting quality.*—Unknown.

Reproductive Organs

Stamens:
*Anthers.*—3 mm.
*Filaments.*—Length:0.9–1.0 cm. Color: White
*Pollen.*—Golden brown.
Pistils:
*Nunber.*—One.
*Length.*—1.3–1.5 cm.
*Stigma.*—Color: Red-purple group 60C; 5–7 parted.
*Style.*—Length:0.8–1.0 cm.
Ovaries:
*Color.*—Green, Pubescent; Superior.
*Length.*—5–6 mm.
Fruit: None General Characteristics Maiden orange is one of three colors in the new Maiden regal Geranium series. The Regal "Maiden" Series is a group of *Pelargonium×domesticum* varieties having large blooms with a compact medium plant size making them suitable for growing in a 13 cm pot. This series exhibits unique plant size, bloom size, and bloom color with a noticeable blotch on only the top two petals instead of all. The series also has demonstrated improved cutting production and rooting times.

I claim:

1. A new and distinct variety of Geranium plant, substantially as shown and described.

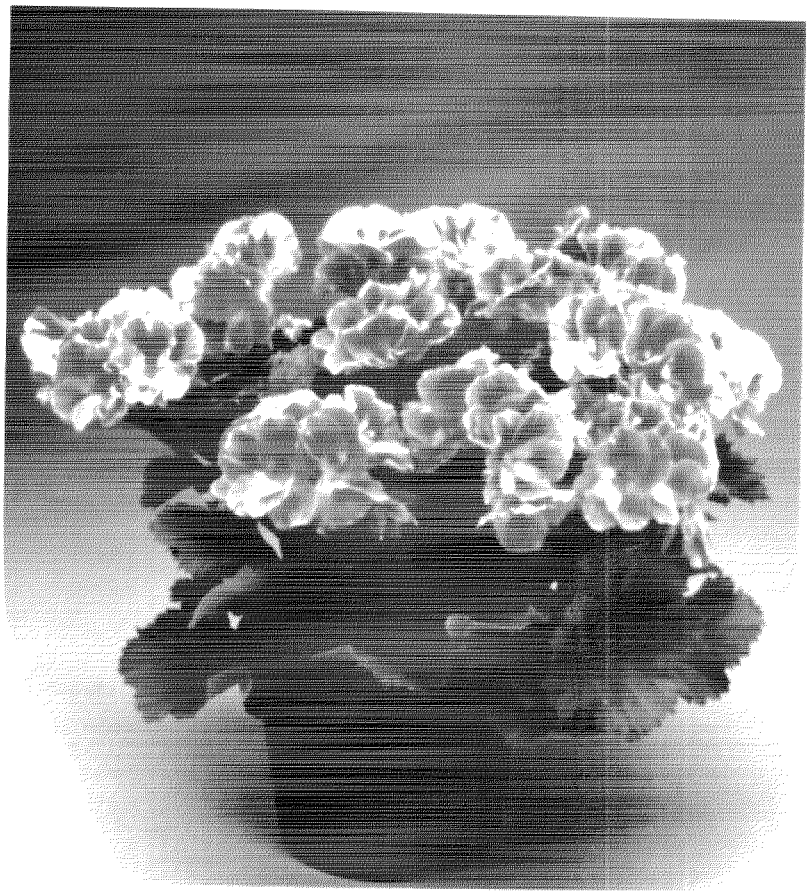

* * * * *